(12) United States Patent
Kim et al.

(10) Patent No.: US 8,309,775 B2
(45) Date of Patent: Nov. 13, 2012

(54) METHOD OF PREPARING IODINATED AROMATIC COMPOUNDS

(75) Inventors: Han-Seok Kim, Gyeonggi-do (KR); Jae-Bong Lim, Geyonggi-do (KR); Il-Hoon Cha, Gyeonggi-do (KR)

(73) Assignee: SK Chemicals Co., Ltd. (KR)

( * ) Notice: Subject to any disclaimer, the term of this patent is extended or adjusted under 35 U.S.C. 154(b) by 356 days.

(21) Appl. No.: 12/599,400

(22) PCT Filed: Dec. 17, 2008

(86) PCT No.: PCT/KR2008/007483
§ 371 (c)(1),
(2), (4) Date: Nov. 9, 2009

(87) PCT Pub. No.: WO2009/078667
PCT Pub. Date: Jun. 25, 2009

(65) Prior Publication Data
US 2010/0222617 A1    Sep. 2, 2010

(30) Foreign Application Priority Data

Dec. 17, 2007   (KR) .................. 10-2007-0132303

(51) Int. Cl.
*C07C 17/00* (2006.01)
(52) U.S. Cl. .................................................. 570/206
(58) Field of Classification Search .............. 570/206
See application file for complete search history.

(56) References Cited

U.S. PATENT DOCUMENTS

| 4,778,938 A | 10/1988 | Rule et al. |
| 4,778,940 A | 10/1988 | Rule et al. |
| 4,792,642 A | 12/1988 | Rule et al. |
| 4,810,826 A | 3/1989 | Cook et al. |
| 5,082,982 A | 1/1992 | Yount et al. |

FOREIGN PATENT DOCUMENTS

| EP | 0183579 | 10/1984 |
| EP | 0181790 | 5/1986 |
| WO | WO 88/02358 | 4/1988 |

OTHER PUBLICATIONS

International Search Report prepared by the Korean Intellectual Property Office on Jul. 24, 2009, for International Application No. PCT/KR2008/007483.
Written Opinion prepared by the Korean Intellectual Property Office on Jul. 24, 2009, for International Application No. PCT/KR2008/007483.
Extended Search Report for European Patent Application No. 08860984.7, dated Jan. 25, 2012, 5 pages.

*Primary Examiner* — Jafar Parsa
(74) *Attorney, Agent, or Firm* — Sheridan Ross P.C.

(57) ABSTRACT

The present invention relates to a method of preparing iodinated aromatic compounds, and more preferably a method of preparing iodinated aromatic compounds comprising a step of iodinating a react ant including an aromatic compound, a di-iodo aromatic compound or water, and iodine (I2) in the presence of a zeolite catalyst and oxygen. The method of the present invention has an advantage that by iodination of a reactant including the aromatic compound, and the di~ iodo aromatic compound or water in the presence of the zeolite catalyst and oxygen, the temperature of the iodinating reactor can be controlled reliably and constantly, thereby resulting in improved productivity per unit weight of catalyst and inhibition of a side reaction in accordance with suppression of producing impurities. In addition, the productivity of the iodinated aromatic compound, preferably the di-iodo aromatic compound, more preferably a p-di-iodo aromatic compound can be improved, and thus can be widely used in the preparation of a di-iodo aromatic compound such as a p-di-iodo aromatic compound.

8 Claims, 4 Drawing Sheets

METHOD OF PREPARING IODINATED AROMATIC COMPOUNDS

BACKGROUND OF THE INVENTION (a) Field of the Invention

The present invention relates to a method of preparing iodinated aromatic compounds, and more specifically to a method of preparing iodinated aromatic compounds comprising: subjecting a mixture including an aromatic compound, a di-iodo aromatic compound or water, and iodine ($I_2$) to iodination in the presence of a zeolite catalyst and oxygen.

(b) Description of the Related Art

The preparation method of the halogenated aromatic compounds using reactants including an aromatic compound such as benzene or naphthalene, and a halogen (bromine, chlorine, iodine, etc.) has been focused on throughout the industrial field. Specifically, among the above halogenated aromatic compounds, p-di-iodo benzene (p-DIB) is widely used as the reactant for the manufacture of polyphenylene sulfide (PPS), and it is commercially valuable, and accordingly studies on improving the productivity of p-DIB have been actively carried out.

For example, as shown in FIG. 1, U.S. Pat. No. 4,778,938 and U.S. Pat. No. 4,746,758 disclose a preparation method of p-DIB using benzene and iodine ($I_2$) as reactants in the presence of a zeolite catalyst and oxygen. According to those prior arts, these preparation methods have advantages in conversion rate in p-DIB productivity. Further, according to the disclosure of the above prior arts, these methods can also minimize the oxidation reaction of the benzene or naphthalene.

However, the above method has a disadvantage in controlling the iodinating reactor temperature, which is related to a locally occurring massive exothermic reaction. As a general rule, the oxidation of the hydrogen iodide (hydroiodic acid, HI) is necessarily accompanied with iodination of aromatic compounds in the presence of a zeolite catalyst and oxygen. This oxidation of HI is a massive exothermic reaction, and thus elevates the temperature of the center of the iodinating reactor. Under this elevated temperature condition, not only the iodination, but also the combustion reaction of reactants is vigorous, and thus brings about a massive runaway reaction. Furthermore, when applying these preparation methods to the plant scale and designing said plant, temperature control becomes more important and is preferentially considered, because the diameter of the reactor should be designed to be sufficiently large.

In addition, under this elevated temperature condition, combustion reaction of the reactants, in accordance with formation of impurities such as carbon deposits, make the catalyst inactive and thus shorten the replacement period of the catalyst. Further, due to the difficulty in controlling the temperature of the iodinating reactor, the feeding flux of the reactants cannot be increased, and a drop in productivity occurs.

SUMMARY OF THE INVENTION

To resolve the problems of the above conventional methods, the present invention provides a method of preparing iodinated aromatic compounds, which can control the temperature of an iodinating reactor reliably and constantly, thereby can improve productivity per unit weight of catalyst and inhibit a side reaction in accordance with suppressing impurity formation.

An embodiment of the present invention relates to a method of preparing iodinated aromatic compounds comprising:

subjecting a mixture including an aromatic compound, a di-iodo aromatic compound or water, and iodine ($I_2$) to iodination in the presence of a zeolite catalyst and oxygen.

The aromatic compounds can be selected form the group consisting of benzene, naphthalene, and biphenyl.

Further, the di-iodo aromatic compound can be selected from the group consisting of di-iodo benzene, di-iodo naphthalene, and di-iodo biphenyl.

To control the temperature of an iodinating reactor reliably and constantly, the di-iodo aromatic compound and the water can be used at a molar ratio of 2 to 10 mole %, and 5 to 30 mole % with regard to the aromatic compound, respectively.

Further, the zeolite catalyst can be selected from the group consisting of Na-13X zeolite, Y-type zeolite, ZSM5 zeolite, and K-13X zeolite.

More preferably, the zeolite catalyst can be Na-13X.

In addition, the iodinating reaction can be conducted at 230 to 350° C. and normal pressure to 5 atm.

The method of the present invention may further comprises:

recycling the di-iodo aromatic compound of a p-di-iodo aromatic compound, an o-di-iodo aromatic compound, and an m-di-iodo aromatic compound, wherein the di-iodo aromatic compound is obtained by distilling the iodination product from the mixture including the aromatic compound, the di-iodo aromatic compound or water, and the iodine ($I_2$), and subjecting the distillate to crystallization and solid-liquid separation.

The method of preparing iodinated aromatic compounds of the present invention can further comprises:

transporting the iodination products from the mixture including the aromatic compound, the di-iodo aromatic compound or water, and the iodine to a first distillation column (C10) from an iodinating reactor (R01), and then separating and recovering the aromatic compound and water from the iodination product at the upper part of the first distillation column (C10);

transporting a distillate from the lower part of the first distillation column (C10) to a second distillation column (C20), and then separating and recovering the mono-iodo aromatic compound and the iodine from the distillate at the upper part of the second distillation column (C20);

transporting a distillate from the lower part of the second distillation column (C20) to a third distillation column (C30), and then separating and recovering the p-di-iodo aromatic compound, the o-di-iodo aromatic compound, and the m-di-iodo aromatic compound from the distillate at the upper part of the third distillation column (C30), and transporting them to a crystallization and solid-liquid separator (D10):

separating and recovering the solid phase p-di-iodo aromatic compound and a mother liquor comprising the liquid phase p-di-iodo aromatic compound, the o-di-iodo aromatic compound, and the m-di-iodo aromatic compound from the crystallization and solid-liquid separator (D10); and recycling the di-iodo aromatic compound by inputting a portion of the mother liquor to the iodinating reactor (R01).

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF MARKS IN THE FIGURES

R01: iodinating reactor C10: first distillation column
C20: second distillation column C30: third distillation column
D10: crystallization and solid-liquid separator

DETAILED DESCRIPTION OF THE EMBODIMENTS

These and other objects of the invention will be more fully understood from the following description of the invention, the referenced drawings attached hereto, and the claims appended hereto.

However, the present invention is not restricted to the following examples, but rather the various embodiments and these examples are provided to describe the present invention, and the present invention is only defined by the claims.

Hereunder is given a detailed description of the present invention.

The method of the present invention has an advantage that by subjecting a mixture including an aromatic compound, a di-iodo aromatic compound or water, and iodine ($I_2$) to iodination in the presence of a zeolite catalyst and oxygen, the temperature of an iodinating reactor can be controlled reliably and constantly, and can thereby improve productivity of an iodinated aromatic compound per unit weight of catalyst and inhibit side reactions in accordance with suppressing impurity formation.

In addition, by further comprising multi-steps of distillation, crystallization, and solid-liquid separation in the embodiment of the present invention, di-iodo aromatic compounds obtained from the method of the present invention can be recycled.

An "aromatic compound" of the present invention is defined as a non-halogenated aromatic compound such as benzene, naphthalene, and biphenyl, and a "mono-iodo aromatic compound" or a "mono-iodo compound" is defined as one in which one hydrogen atom of the aromatic compound is substituted by the iodine atom, such as mono-iodo benzene.

In addition, a "di-iodo aromatic compound" or a "di-iodo compound" is defined as one in which any two hydrogen atoms of the aromatic compound are substituted by iodine atoms, such as di-iodo benzene. Further, a di-iodo aromatic compound has three kinds of isomers, which are a p-di-iodo aromatic compound, an o-di-iodo aromatic compound, and a m-di-iodo aromatic compound. In addition, an "iodinated aromatic compound", which is to be prepared in the present invention, is defined as one in which more than one hydrogen atom in the aromatic compound is substituted by an iodine atom, comprising a mono-iodo aromatic compound, a di-iodo aromatic compound, and a tri-iodo aromatic compound.

Further, "iodination" of the present invention is defined as a reaction of an aromatic compound such as benzene and naphthalene with iodine ($I_2$), so as to substitute a hydrogen atom of the aromatic compound to an iodine atom. From the iodination, the mono-iodo aromatic compound and a multi-iodo aromatic compound, such as a di-iodo aromatic compound, and a tri-iodo aromatic compound, can be obtained.

Figure 2:
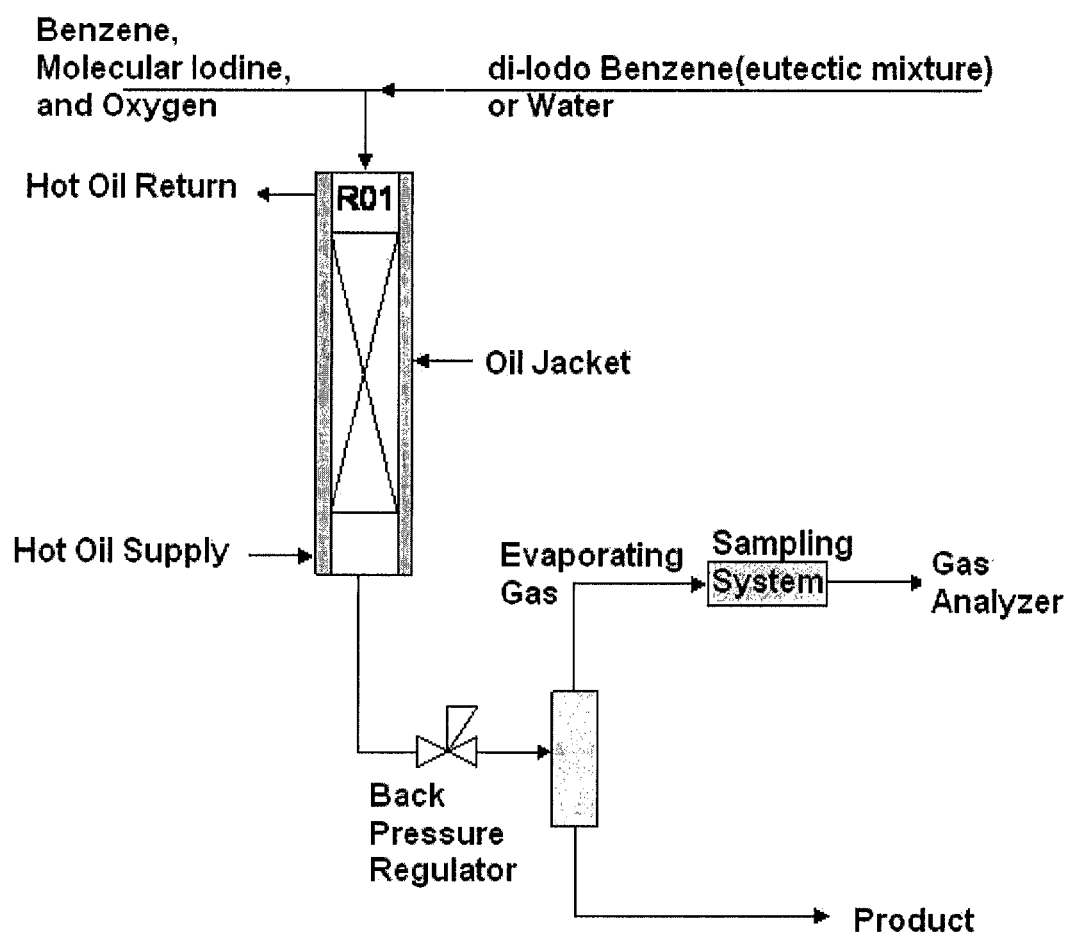
FIG. 2 is a schematic drawing showing the preparation method of iodinated aromatic compounds according to Examples 1 and 2.

Referring to FIG. 2, the preparation method of the present invention has an advantage that, by subjecting a mixture including an aromatic compound, a di-iodo aromatic compound or water, and iodine ($I_2$) to iodination in the presence of a zeolite catalyst and oxygen, the temperature of the iodinating reactor can be controlled reliably and constantly, and thereby can improve productivity of the iodinated aromatic compound.

One embodiment of the present invention relates to a preparation method of iodinated aromatic compounds comprising:

subjecting a mixture including an aromatic compound, a di-iodo aromatic compound or water, and iodine ($I_2$) to iodination in the presence of a zeolite catalyst and oxygen.

That is to say, in accordance with the above embodiment of the present invention, by adding a di-iodo aromatic compound to an aromatic compound that is subject of the iodination with iodine ($I_2$), a side reaction caused by the iodinated aromatic compound such as a mono-iodo aromatic compound and di-iodo aromatic compound can be suppressed, and can thereby control the temperature of the iodinating reactor reliably and constantly. Further, by suppressing a side reaction of the iodinated aromatic compound such as the mono-iodo aromatic compound and the di-iodo aromatic compound, both the productivity of the iodinated aromatic compound (especially, di-iodo aromatic compound) and the selectivity of the commercially valuable p-di-iodo aromatic compound can be significantly increased.

According to one example of the above embodiment of the present invention, by adding water to an aromatic compound that is subject of iodination with iodine ($I_2$), an oxidation reaction of hydrogen iodide (intense exothermic reaction) can be controlled reliably, and accordingly the temperature of an iodinating reactor can be controlled reliably and constantly.

Therefore, by adding the di-iodo aromatic compound or water to the aromatic compound that is subject of iodination with iodine ($I_2$) according to any one of embodiments of the present invention, productivity of the di-iodo aromatic compound and selectivity of a p-di-iodo aromatic compound can be maintained to be high. Further, the temperature of the iodinating reactor can be controlled reliably and constantly, and accordingly the feeding flux of the reactants can be increased, and thus productivity of the commercially valuable p-di-iodo aromatic compound can be increased.

As a general rule, iodination of an aromatic compound in the presence of a zeolite catalyst is accompanied with adsorption and desorption of reactants and products. Concretely, reactants are adsorbed on a zeolite catalyst and then desorbed in the form of an iodinated aromatic compound after iodination. On average, the adsorption/desorption is vigorous in the upper part of the iodinating reactor. Therefore, heat of reaction is developed locally, and accordingly the temperature of the reactor is locally high. However, according to the present invention, the adsorption/desorption is carried out evenly throughout the reactor, and can thereby control the temperature of an iodinating reactor reliably and constantly and suppress a side reaction caused by the increased temperature.

In addition, according to the present invention, the production of carbon dioxide and carbon deposits can be minimized, and thereby the period for zeolite catalyst replacement can be extended. Further, according to the present invention, productivity of commercially valuable iodinated aromatic compound can be increased.

In the iodination of the above embodiment of the present invention, the presence of oxygen is essential. Hydrogen iodide obtained in the iodination should be oxidized to iodine ($I_2$) to participate in the iodination again. Therefore, in the absence of oxygen or when only a minor amount of oxygen is present in comparison with that of hydrogen iodide, the hydrogen iodide with water from the oxidation reaction form a common ratio and have a harmful effect one the refining process and can corrode the apparatus by an intense oxidation reaction.

The back pressure regulator shown in FIG. 2 controls the reaction pressure of iodination and makes the pressurization reaction possible. The sample handling system shown in FIG. 2 removes vapor included in the gas to protect a gas analyzer. Further, the gas analyzer can be used to analyze the concentration of carbon dioxide in the gas.

The zeolite catalyst of the present invention can be selected form the group consisting of Y-type zeolite, ZSM5 zeolite, and K-13X zeolite, but is not limited to them, and can preferably be Na-13X zeolite.

In addition, the aromatic compound of the present invention can be preferably selected from the group consisting of benzene, naphthalene, and biphenyl, and the di-iodo aromatic compound of the present invention can be preferably selected from the group consisting of di-iodo benzene, di-iodo naphthalene, and di-iodo biphenyl.

The molar ratio of the aromatic compound with regard to iodine ($I_2$) can be varied according to the reaction conditions. If a large quantity of the iodine ($I_2$) is used, the productivity of the multi-iodinated aromatic compound is increased while the conversion rate of the iodine ($I_2$) is lower. However, if a large quantity of the aromatic compound with respect to the iodine ($I_2$) is used in order to increase the conversion rate of the iodine ($I_2$), the conversion rate of the iodine ($I_2$) can be increased, while the productivity of the di-iodo aromatic compound is decreased. Therefore, considering the object of the iodination, the molar ratio of the aromatic compound to iodine ($I_2$) can be appropriately controlled, and preferably it can be used at a molar ratio of 0.3 to 3.0 (aromatic compound/iodine).

In addition, the di-iodo aromatic compound can be used at a molar ratio of 2 to 10 mole % with regard to the aromatic compound, and the water can be used at a molar ratio of 5 to 30 mole % with regard to the aromatic compound.

Further, the water can be tap water or distilled water, but is not limited to these.

According to the temperature profile in accordance with the iodination of one example of the present invention, when the reaction temperature was adjusted higher, the conversion rates of the reactants (aromatic compound and iodine) were higher, while the selectivity of the commercially valuable p-di-iodo aromatic compound was lower. In addition, the reaction pressure can be adjusted within various pressure ranges. When the reaction pressure is adjusted higher, iodinating reaction efficiency can be increased. Considering the above, the iodination can be preferably conducted at 230 to 350° C. and normal pressure to 5 atm.

In addition, the di-iodo aromatic compound can be obtained according to a general preparation method or by purchasing one that is commercially prepared, but is not limited to these. And, it can preferably be obtained according to another embodiment of the present invention further comprising multi-steps such as distillation, recrystallization, and solid-liquid separation from a reaction product of iodination whose reactants are the aromatic compound, the di-iodo aromatic compound or water, and the iodine ($I_2$). Further, said di-iodo aromatic compound includes three kinds of isomers of a p-di-iodo aromatic compound, an o-di-iodo aromatic compound, and a m-di-iodo aromatic compound.

Figure 3:
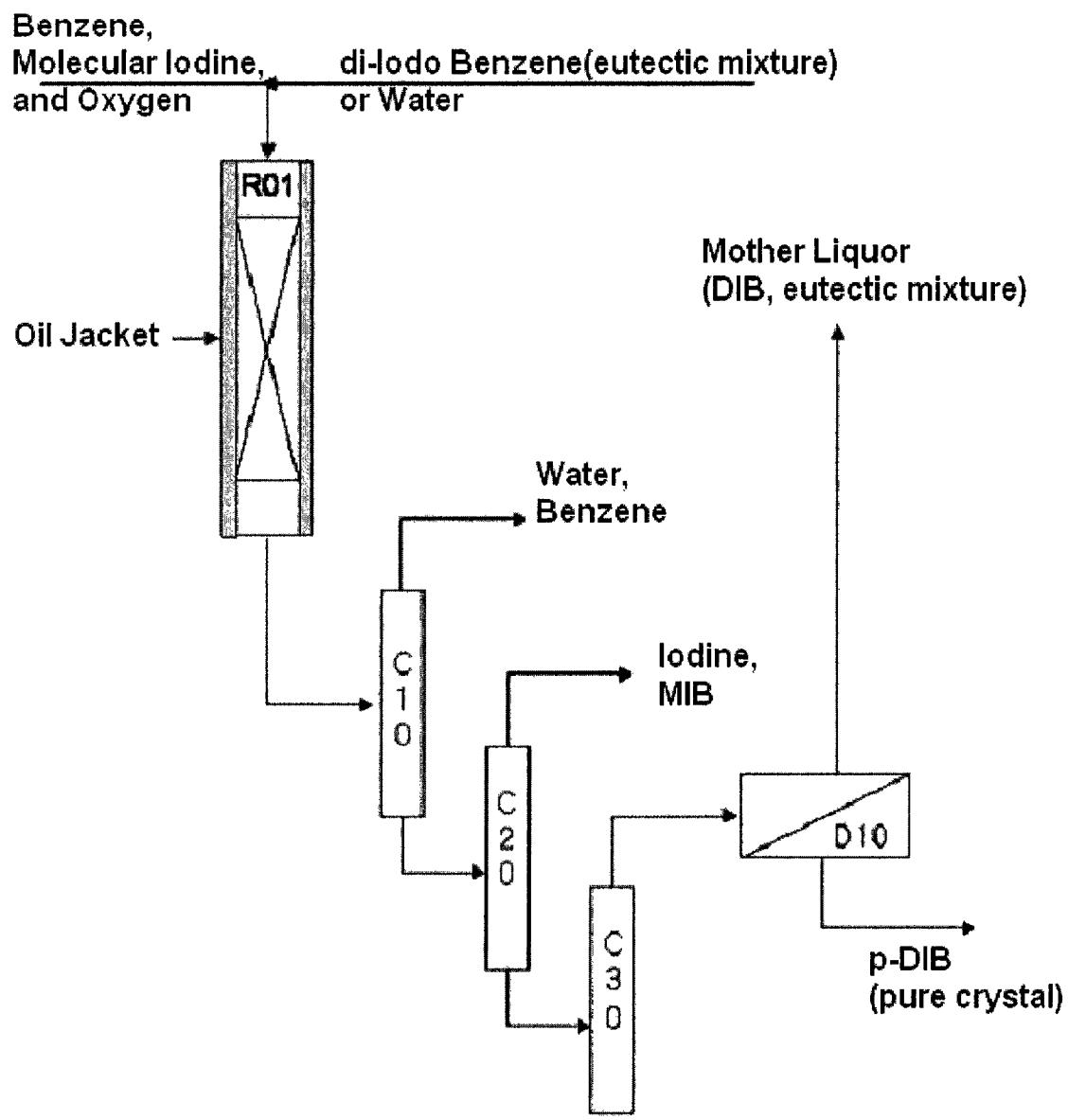
FIG. 3 is a schematic drawing showing the method of preparing iodinated aromatic compounds and recycling of the di-iodo aromatic compounds being an eutectic mixture, according to one embodiment of the present invention.

Referring to FIG. 3, the preferred embodiment of preparation method further comprises a method of recycling the di-iodo aromatic compound, and the method of recycling may comprise:

transporting the iodination product from the mixture including the aromatic compound, the di-iodo aromatic compound or water, and the iodine ($I_2$) to a first distillation column (C10) from an iodinating reactor (R01), and then separating and recovering the aromatic compound and water from the iodination product at the upper part of the first distillation column (C10);

transporting a distillate from the lower part of the first distillation column (C10) to a second distillation column (C20), and then separating and recovering a mono-iodo aromatic compound and iodine ($I_2$) from the distillate at the upper part of the second distillation column (C20);

transporting a distillate from the lower part of the second distillation column (C20) to a third distillation column (C30), and then separating and recovering a di-iodo aromatic compound including a p-di-iodo aromatic compound, an o-di-iodo aromatic compound, and an m-di-iodo aromatic compound from the distillate at the upper part of the third distillation column (C30), and the transporting them to a crystallization and solid-liquid separator (D10);

separating and recovering the solid phase p-di-iodo aromatic compound and a mother liquor comprising the liquid phase p-di-iodo aromatic compound, the o-di-iodo aromatic compound, and the m-di-iodo aromatic compound from the crystallization and solid-liquid separator (D10); and recycling the di-iodo aromatic compound by inputting a portion of the mother liquor to the iodinating reactor (R01).

The melting points of the p-di-iodo benzene, the m-di-iodo benzene, and the o-di-iodo benzene are 131° C., 36° C., and 27° C., respectively. Therefore, the obtained di-iodo benzene from the upper part of the third distillation column (C30) was present in the form of liquid and solid mixture (eutectic mixture) at normal temperature (25° C.), according to one example of the present invention. Concretely, after recrystallization and separation, a mother liquor comprising 15.4% of p-di-iodo benzene, 71.5% of m-di-iodo benzene, and 15.4% of o-di-iodo benzene could be separated from pure solid p-di-iodo benzene. From these, three kinds of isomers (p-, m-, o-) form a eutectic mixture at a lower temperature than the melting points of the three kinds of isomers, and can thereby be present in the form of a liquid at normal temperature. By recycling the above di-iodo benzene from the mother liquor to the iodinating reactor (R01), one of the objects of the present invention can be resolved.

Figure 4:
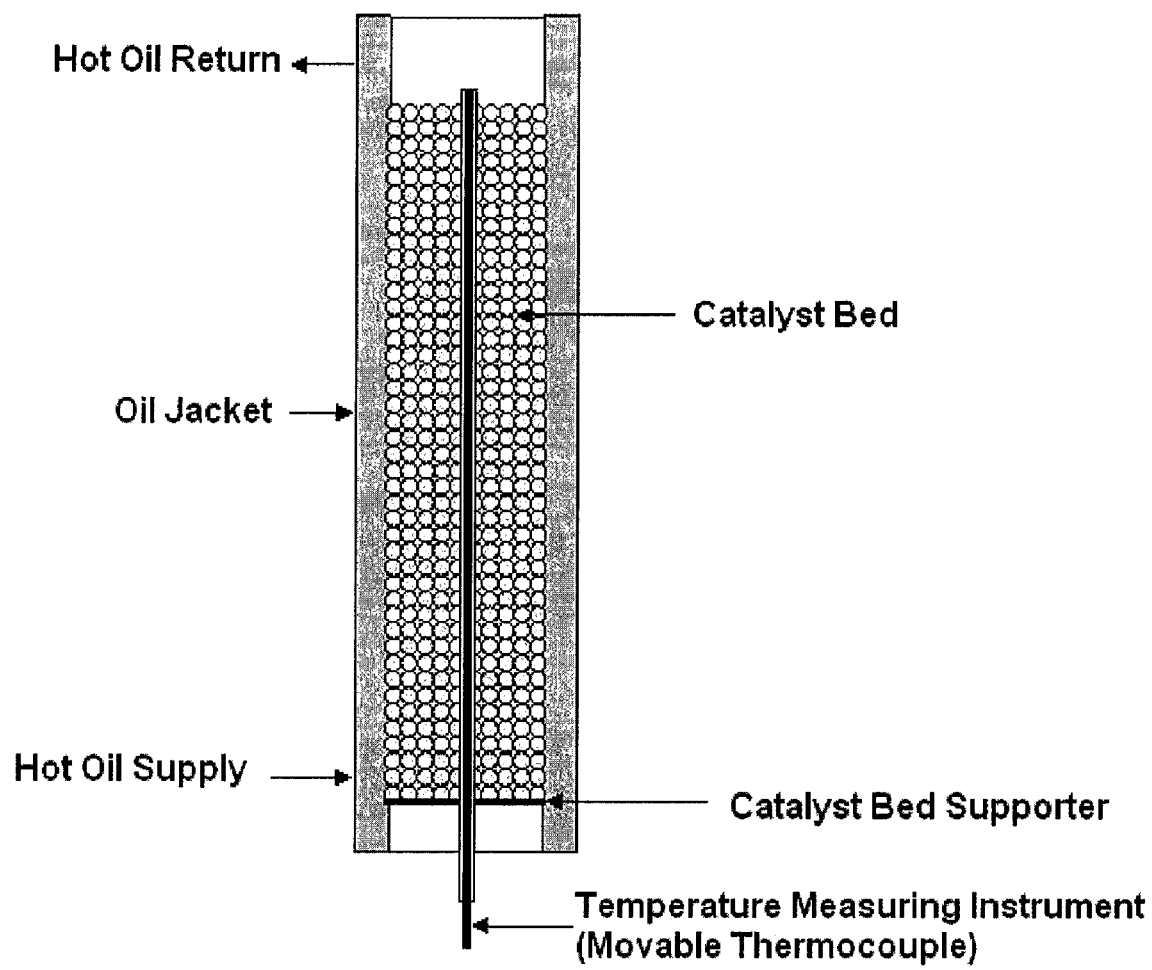
FIG. 4 is a detail drawing of the iodinating reactor (R01).

Furthermore, FIG. 4 is a detail drawing of the iodinating reactor (R01), which is also shown in FIG. 2 and FIG. 3. FIG. 4 concretely shows the catalyst bed in the inner part of the iodinating reactor (R01), and a movable thermocouple. The zeolite catalyst is packed in the inner part of the iodinating reactor (R01), surrounded by a catalyst bed supporter and an oil jacket. In addition, a movable thermocouple is installed in the inner part of the catalyst bed, as shown in FIG. 4. To maintain the reaction temperature to be constant, oil can be supplied from the lower part of the oil jacket, and it absorbs elevated heat of the iodinating reaction and recycles it to the upper part of the oil jacket where it is recovered. As set forth above, by recycling and recovering oil through the oil jacket, the reaction temperature of the iodinating reactor can be controlled reliably and constantly.

The present invention is further explained in more detail with reference to the following examples. These examples, however, should not be interpreted as limiting the scope of the present invention in any manner.

Hereunder is given the terms used in the following comparative examples and examples to prove the usefulness of the present invention.

First of all, the ratio of "aromatic/I" describes the molar ratio of the aromatic compound to the iodine being used. Concretely, to prepare di-iodo benzene, benzene should react with 1 mole of iodine (2 iodine atoms, $I_2$). Therefore, the aromatic/I is defined as in the following Equation 1.

$$\text{Aromatic}/I=[(\text{number of moles of benzene}\times 2)+(\text{number of moles of mono-iodo benzene})]/\text{iodine }(I_2)\times 2 \quad \text{[Equation 1]}$$

Further, the terms used to prove the usefulness of the reaction products and the process are as below. First of all, the productivity of p-DIB is defined as the production rate of p-DIB per unit time and unit volume of the catalyst, and its unit is expressed as g/l·hr. The conversion rate of the iodine ($I_2$) and benzene is defined as the amount of the converted iodine ($I_2$) or benzene to the amount of the iodine ($I_2$) or benzene, and the ratio is expressed as a percentage (%).

The iodinated benzene produced by the iodination comprises mono-iodo benzene (MIB), di-iodo benzene (DIB), and tri-iodo benzene (TIB), and DIB and TIB can have three kinds of isomers, respectively. Concretely, DIB has three kinds of isomers of p-di-iodo benzene (p-DIB), o-di-iodo benzene (o-DIB), and m-di-iodo benzene (m-DIB). In addition, "Total DIB" can be defined as the total weight percentage of the produced p-DIB, o-DIB, and m-DIB with regard to the product, and is expressed as in the following Equation 2.

$$\text{Total }DIB=(p\text{-}DIB+m\text{-}DIB+o\text{-}DIB)/(\text{Product})\times 100 \quad \text{[Equation 2]}$$

Further, the selectivity can be defined as weight percentage of p-DIB with regard to the three kinds of DIB produced, and is expressed as in the following Equation 3.

$$\text{Selectivity}=(p\text{-}DIB)/(p\text{-}DIB+m\text{-}DIB+o\text{-}DIB)\times 100 \quad \text{[Equation 3]}$$

According to the present invention, the commercially valuable p-di-iodo aromatic compound can be produced effectively, and this results from the high "Total DIB" and "selectivity of p-DIB".

Comparative Example 1

Figure 1:
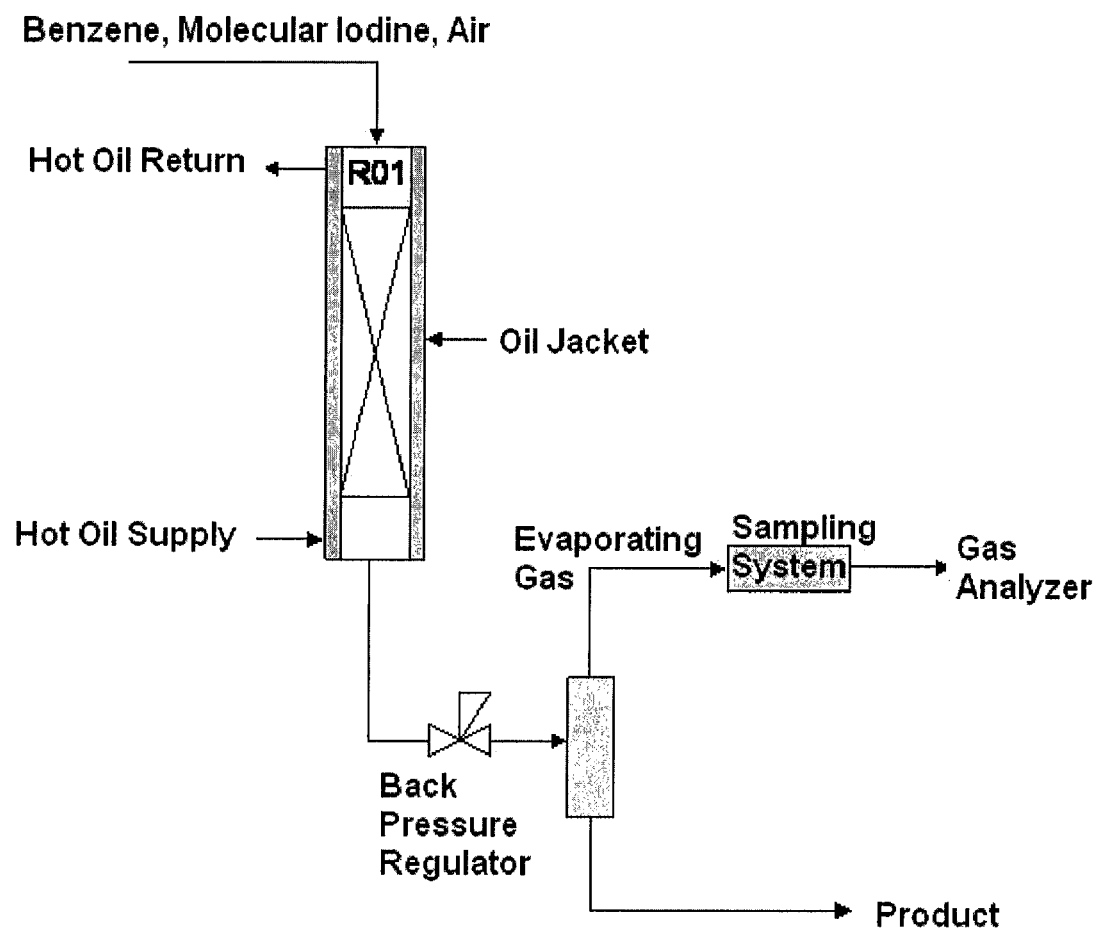
FIG. 1 is a schematic drawing showing the preparation method of iodinated aromatic compounds according to the Comparative Examples 1 and 2.

The iodinating reactor shown in FIG. 1 was used, and without adding DIB, only the benzene (176.4 g/hr), iodine ($I_2$) (275.0 g/hr), and air were reacted. The iodine ($I_2$) and the air went through the preheater and were heated to 200° C. and then supplied to the iodinating reactor (R01). Further, benzene was also heated to 200° C. and supplied in the form of a vapor, using the other feeding line. The reaction temperature of the iodinating reactor was controlled by controlling the temperature of oil supplied to the oil jacket. And the temperature of the iodinating reactor, which was measured at the inner center of the reactor, was adjusted to be constant at 280° C. Nevertheless, the reaction temperature was not maintained constantly. The temperature of the upper part of the iodinating reactor was higher than preferable. And, the temperature of the iodinating reactor went down along with the flow direction of the reactant. To examine temperature profile of the iodinating reactor, a temperature measuring instrument such as a thermowell and a thermocouple was installed at the inner center of the iodinating reactor. The temperature of the upper, middle, and lower parts of the iodinating reactor was then periodically examined using the movable thermocouple, which can move upward and downward of the iodinating reactor to determine the highest temperature region. The reaction was carried out in the normal temperature for 24 hours after reaching the reaction condition. Then, sampling and analyzing were conducted after the iodination, and the reaction conditions and results are shown in the following Table 1.

Comparative Example 2

Except that the benzene and iodine ($I_2$) were supplied at 265.2 g/hr and 412.5 g/hr respectively, all of the reaction conditions were adjusted to be the same as in Comparative Example 1. In Comparative Example 2, the reliable and constant control of the reaction temperature also failed. That is to say, the temperature in the upper part of the iodinating reactor was elevated to more than 380° C., and thus the reaction was stopped. When the reaction temperature is higher than the above, a massive runaway reaction of the benzene can be brought about, which then results in massive deposits of carbon compounds.

Example 1

The iodinating reactor shown in FIG. 2 was used, and except that the benzene (565.2 g/hr), di-iodo benzene (83.4 g/hr), and iodine ($I_2$) (900.1 g/hr) were supplied to the iodinating reactor (R01), all of the reaction conditions were adjusted to be the same as in Comparative example 1. The reaction conditions and reaction results are shown in the following Table 1. The used DIB was obtained from a mother liquor of three kinds of isomers (p-, o-, and m-), which was separated from pure crystallized solid p-DIB.

Example 2

Except that the benzene, water, and iodine ($I_2$) were supplied at 550.0 g/hr, 35 g/hr, and 744.1 g/hr, respectively, all of the reaction conditions were adjusted to be the same as in Comparative Example 1. The reaction conditions and the reaction results are shown in the following Table 1.

TABLE 1

|  |  | Comparative Example 1 | Comparative Example 2 | Example 1 | Example 2 |
| --- | --- | --- | --- | --- | --- |
| Benzene | g/hr | 176.4 | 265.2 | 565.2 | 550.0 |
| Iodine | g/hr | 275.0 | 412.5 | 900.1 | 744.1 |
| Aromatic/I | Molar ratio | 2.08 | 2.09 | 2.04 | 2.40 |
| DIB | g/hr | 0 | 0 | 83.4 | 0 |
| Water ($H_2O$) | g/hr | 0 | 0 | 0 | 35 |
| Benzene | Wt % | 14.96 |  | 12.56 | 16.71 |
| MIB | Wt % | 50.40 |  | 40.99 | 45.31 |
| p-DIB | Wt % | 22.33 |  | 30.69 | 22.06 |

TABLE 1-continued

|  |  | Comparative Example 1 | Comparative Example 2 | Example 1 | Example 2 |
|---|---|---|---|---|---|
| m-DIB | Wt % | 5.76 |  | 4.88 | 5.59 |
| o-DIB | Wt % | 1.12 |  | 1.45 | 1.86 |
| TIB | Wt % | 1.72 |  | 2.13 | 3.22 |
| Productivity of p-DIB | g/l · hr | 13.80 |  | 64.24 | 40.74 |
| Conversion rate of $I_2$ | % | 97.64 |  | 94.84 | 97.81 |
| Conversion rate of benzene | % | 63.33 |  | 67.44 | 60.64 |
| Total DIB | Wt % | 30.33 |  | 39.93 | 31.14 |
| Selectivity of p-DIB | % | 76.45 |  | 82.90 | 74.75 |
| Carbon deposits | g/kg | 0.78 |  | 0.64 | 0.59 |
| $CO_2$ | % | 2.33 |  | 1.07 | 0.98 |

As shown in Table 1, there are little differences between the comparative examples and examples regarding total DIB, selectivity of p-DIB, and conversion rate of the reactant. As set forth above, as the reactants except iodine ($I_2$), Comparative Example 1 only used benzene, Example 1 used benzene and DIB, and Example 2 used benzene and water, respectively. While total DIB, selectivity, and conversion rate of the comparative examples and examples are nearly alike, the productivity of the p-DIB of the examples is much higher than that of the comparative examples. Concretely, the p-DIB productivity of Example 1 or 2 is 3 times higher than that of Comparative Example 1. This may result from the control of the iodinating reactor temperature. To elevate p-DIB productivity, the input rate of the feeding reactant should be increased. However, as shown in the reaction results of Comparative Example 2, in the case that the reactant is solely benzene and iodine, when the feeding flux of the reactant is increased, the temperature in the upper part of the iodinating reactor is elevated beyond control. According to the temperature profile of Comparative Example 1, the temperature of the upper part was 40° C. higher than that of the center of the iodinating reactor. Further, considering the amount of $CO_2$ and carbon deposits, Examples 1 and 2 are superior to Comparative Examples 1 and 2. This results from the temperature control of the iodinating reactor.

Therefore, the preparation method of the present invention is advantageous in controlling temperature of the iodinating reactor, thereby improving productivity of an iodinated aromatic compound per unit weight of catalyst and improving production of DIB, especially p-DIB, by iodinating a reactant including an aromatic compound, a di-iodo aromatic compound or water, and iodine ($I_2$) with the zeolite catalyst and oxygen. Therefore, the preparation method of the present invention can be widely and effectively used in the manufacture of the iodinated aromatic compound.

What is claimed is:

1. A method of preparing iodinated aromatic compounds, comprising:
    subjecting a gaseous mixture including an aromatic compound, a di-iodo aromatic compound or water, and iodine ($I_2$) to iodination in the presence of a zeolite catalyst and oxygen,
    wherein the di-iodo aromatic compound is used at a molar ratio of 2 to 10 mole % with regard to the aromatic compound, and
    wherein the water is used at a molar ratio of 5 to 30 mole % with regard to the aromatic compound.
2. The method of claim 1,
    wherein the aromatic compound is selected from the group consisting of benzene, naphthalene, and biphenyl.
3. The method of claim 1,
    wherein the di-iodo aromatic compound is selected from the group consisting of di-iodo benzene, di-iodo naphthalene, and di-iodo biphenyl.
4. The method of claim 1,
    wherein the zeolite catalyst is selected from the group consisting of Na-13X zeolite, Y-type zeolite, ZSM5 zeolite, and K-13X zeolite.
5. The method of claim 4,
    wherein the zeolite catalyst is Na-13X zeolite.
6. The method of claim 1,
    wherein the iodination is conducted at 230 to 350° C. and normal pressure to 5 atm.
7. The method of claim 1, further comprising:
    recycling the di-iodo aromatic compound of a p-di-iodo aromatic compound, an o-di-iodo aromatic compound, and a m-di-iodo aromatic compound,
    wherein the di-iodo aromatic compound is obtained by distilling the iodination product from the mixture including the aromatic compound, the di-iodo aromatic compound or water, and the iodine ($I_2$), and subjecting the distillate to crystallization and solid-liquid separation.
8. The method of claim 7, further comprising:
    transporting the iodination product from the mixture including the aromatic compound, the di-iodo aromatic compound or water, and the iodine ($I_2$) to a first distillation column (C10) from an iodinating reactor (R01), and then separating and recovering the aromatic compound and water from the iodination product at the upper part of the first distillation column (C10);
    transporting a distillate from the lower part of the first distillation column (C10) to a second distillation column (C20), and then separating and recovering the mono-iodo aromatic compound and the iodine from the distillate at the upper part of the second distillation column (C20);
    transporting a distillate from the lower part of the second distillation column (C20) to a third distillation column (C30), and then separating and recovering the di-iodo aromatic compound including the p-di-iodo aromatic compound, the o-di-iodo aromatic compound, and the m-di-iodo aromatic compound from the distillate at the upper part of the third distillation column (C30), and then transporting them to a crystallization and solid-liquid separator (D10);
    separating and recovering the solid phase p-di-iodo aromatic compound and a mother liquor comprising the liquid phase p-di-iodo aromatic compound, the o-di-iodo aromatic compound, and the m-di-iodo aromatic compound from the crystallization and solid-liquid separator (D10); and
    recycling the di-iodo aromatic compound by inputting a portion of the mother liquor to the iodinating reactor (R01).

* * * * *